(12) United States Patent
Prabhu Verleker et al.

(10) Patent No.: US 11,207,041 B2
(45) Date of Patent: Dec. 28, 2021

(54) X-RAY CT SYSTEM AND MEDICAL PROCESSING APPARATUS

(71) Applicant: CANON MEDICAL SYSTEMS CORPORATION, Otawara (JP)

(72) Inventors: Akshay Narayan Prabhu Verleker, Nasushiobara (JP); Hiroki Taguchi, Otawara (JP)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 0 days.

(21) Appl. No.: 16/923,565

(22) Filed: Jul. 8, 2020

(65) Prior Publication Data

US 2021/0007691 A1    Jan. 14, 2021

(30) Foreign Application Priority Data

Jul. 8, 2019  (JP) .............................. JP2019-126685
Jun. 23, 2020  (JP) .............................. JP2020-107894

(51) Int. Cl.
*A61B 6/00*    (2006.01)
*A61B 6/03*    (2006.01)
*A61B 6/02*    (2006.01)
*A61B 6/06*    (2006.01)

(52) U.S. Cl.
CPC .............. *A61B 6/482* (2013.01); *A61B 6/027* (2013.01); *A61B 6/032* (2013.01); *A61B 6/06* (2013.01); *A61B 6/4035* (2013.01); *A61B 6/461* (2013.01); *A61B 6/52* (2013.01)

(58) Field of Classification Search
CPC ......... A61B 6/482; A61B 6/027; A61B 6/032; A61B 6/461; A61B 6/4035; A61B 6/06; A61B 6/52; A61B 6/405; A61B 6/465; A61B 6/467; A61B 6/5205; A61B 6/488
See application file for complete search history.

(56) References Cited

U.S. PATENT DOCUMENTS

2008/0232667 A1    9/2008  Kitamura et al.
2014/0050378 A1*   2/2014  Sengupta ............. G01N 23/046
                                                    382/131

FOREIGN PATENT DOCUMENTS

JP     04-347143 A     12/1992
JP     08-294485 A     11/1996
JP     2005-143948 A    6/2005
JP     2008-229161 A   10/2008

* cited by examiner

*Primary Examiner* — Courtney D Thomas
(74) *Attorney, Agent, or Firm* — Oblon, McClelland, Maier & Neustadt, L.L.P.

(57) ABSTRACT

An X-ray CT system according to an embodiment includes processing circuitry configured to: execute first scanning of acquiring a first subject data set corresponding to first X-ray energy by irradiating a first region of a subject with X-rays; execute, after the first scanning, second scanning of acquiring a second subject data set corresponding to second X-ray energy and a third subject data set corresponding to third X-ray energy different from the second X-ray energy by irradiating a second region included in the first region with X-rays; and perform material decomposition among a plurality of reference materials based on: a fourth subject data set obtained based on the first subject data set and one of the second subject data set and the third subject data set; and the other of the second subject data set and the third subject data set.

15 Claims, 7 Drawing Sheets

$\mu_{bone}(E11) \neq \mu_{soft\,tissue}(E11)$

· $\mu_{bone}(E11) \neq \mu_{bone}(E12)$

X-RAY CT SYSTEM AND MEDICAL PROCESSING APPARATUS

CROSS-REFERENCE TO RELATED APPLICATIONS

This application is based upon and claims the benefit of priority from Japanese Patent Application No. 2019-126685, filed on Jul. 8, 2019; and Japanese Patent Application No. 2020-107894, filed on Jun. 23, 2020, the entire contents of all of which are incorporated herein by reference.

FIELD

Embodiments described herein relate generally to an X-ray CT system and a medical processing apparatus.

BACKGROUND

According to an existing technology, material decomposition of an object is performed by using a plurality of reference materials based on projection data corresponding to two or more kinds of X-ray energy and acquired by an X-ray computed tomography (CT) scanner, and a result of the material decomposition is displayed as an image. When two kinds of X-ray energy are used, this technology is called dual energy (DE), and material decomposition between two kinds of reference materials is possible.

For example, with the dual energy technology, it is possible to decompose materials such as a kidney stone, fat, soft tissue, and a bone in the body of a subject. In addition, with the dual energy technology, it is possible to determine whether a kidney stone in the body of the subject is a calcium stone or a uric acid stone.

In some cases, noise and artifacts are included in projection data acquired by an X-ray CT scanner due to various kinds of factors. In particular, when the physical size of a subject is large, an X-ray is likely to attenuate, and decrease of the quality of the projection data is significant. When high-energy and high-radiation-dose X-rays are used, the quality of the projection data improves but the amount of radiation exposure of the subject increases. When the energy of X-rays on the low-energy side in dual energy is increased, the accuracy of material decomposition potentially decreases due to the energy difference decrease.

DETAILED DESCRIPTION

An X-ray CT system includes processing circuitry. The processing circuitry executes first scanning of acquiring a first subject data set corresponding to first X-ray energy by irradiating a first region of a subject with X-rays and executes, after the first scanning, second scanning of acquiring a second subject data set corresponding to second X-ray energy and a third subject data set corresponding to third X-ray energy different from the second X-ray energy by irradiating a second region included in the first region with X-rays. In addition, the processing circuitry performs material decomposition among a plurality of reference materials based on: a fourth subject data set obtained based on the first subject data set and one of the second and third subject data sets; and the other of the second and third subject data sets.

Embodiments of an X-ray CT system and a medical processing apparatus will be described below in detail with the accompanying drawings. An X-ray CT system and a medical processing apparatus according to the present application are not limited by the embodiments described below.

Figure 1:
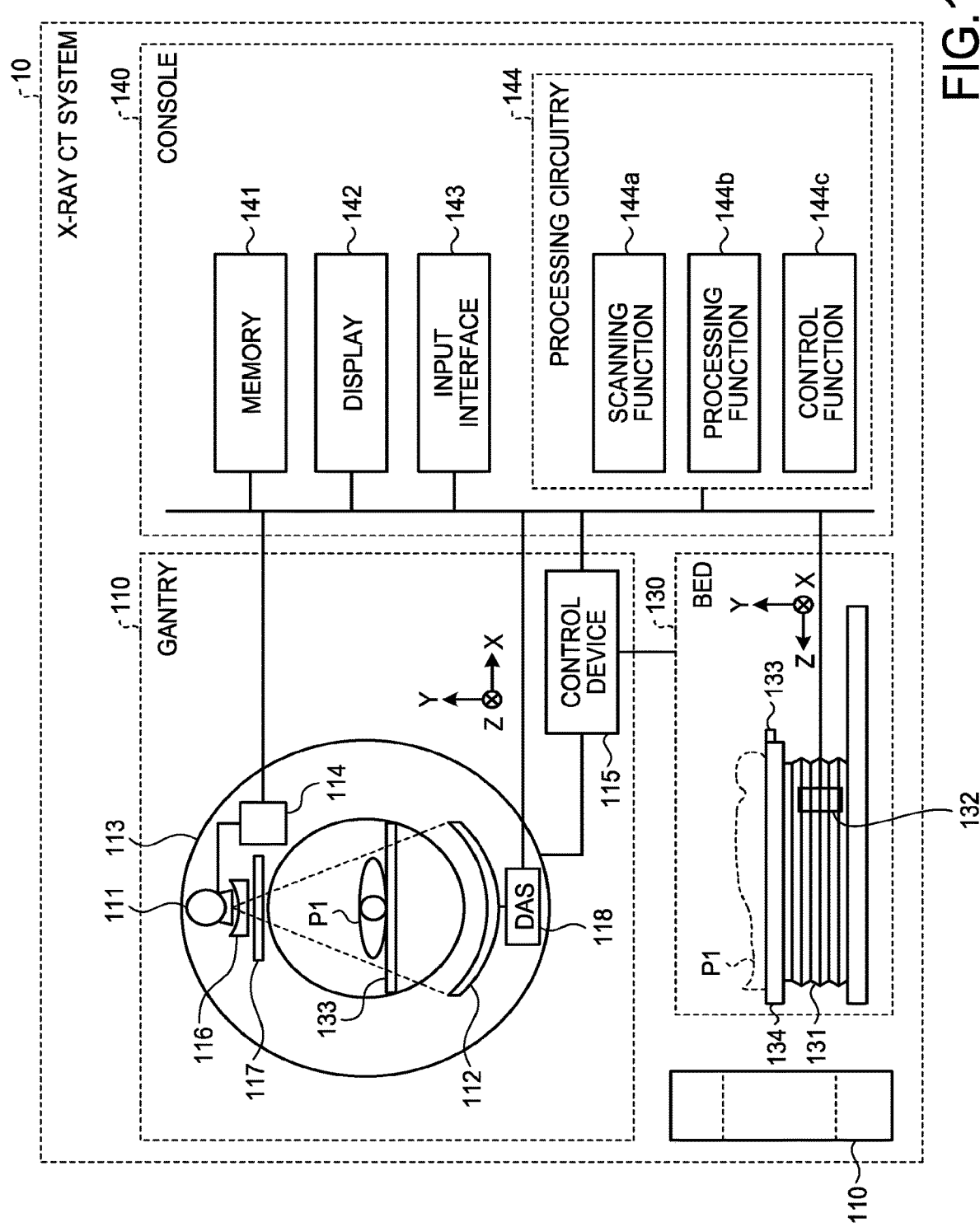
FIG. 1 is a block diagram illustrating an exemplary configuration of an X-ray CT system according to a first embodiment.

The following first describes the configuration of an X-ray CT system 10 according to a first embodiment with reference to FIG. 1. FIG. 1 is a block diagram illustrating an exemplary configuration of the X-ray CT system 10 according to the first embodiment. As illustrated in FIG. 1, the X-ray CT system 10 includes a gantry 110, a bed 130, and a console 140. The X-ray CT system 10 is also called an X-ray CT apparatus or an X-ray CT scanner.

In FIG. 1, a Z-axis direction is defined to be along the rotational axis of a rotation frame 113 not being tilted or the longitudinal direction of a couchtop 133 of the bed 130. An X-axis direction is defined to be orthogonal to the Z-axis direction and horizontal to the floor surface. A Y-axis direction is defined to be orthogonal to the Z-axis direction and vertical to the floor surface. FIG. 1 illustrates the gantry 110 in a plurality of directions for description and corresponds to a case in which the X-ray CT system 10 includes one gantry 110.

The gantry 110 includes an X-ray tube 111, an X-ray detector 112, the rotation frame 113, an X-ray high-voltage device 114, a control device 115, a wedge 116, a collimator 117, and a DAS 118.

The X-ray tube 111 is a vacuum tube including a cathode (filament) generates thermions, and an anode (target) that generates X-rays upon collision with thermions. The X-ray tube 111 receives high-voltage application from the X-ray high-voltage device 114 and emits thermions from the cathode toward the anode, thereby generating X-rays with which a subject P1 is to be irradiated.

The X-ray detector 112 detects X-rays emitted from the X-ray tube 111 and having passed through the subject P1 and outputs a signal corresponding to the amount of detected X-rays to the DAS 118. The X-ray detector 112 includes, for example, a plurality of detection element columns each including a plurality of detection elements arrayed in a channel direction along one arc centered at a focal point of the X-ray tube 111. The X-ray detector 112 has a structure in which, for example, a plurality of detection element columns each including a plurality of detection elements arrayed in the channel direction are arrayed in a column direction (slice direction or row direction).

For example, the X-ray detector 112 is an indirect conversion detector including a grid, a scintillator array, and a light sensor array. The scintillator array includes a plurality of scintillators. Each scintillator includes a scintillator crystal that outputs light in the amount of photons in accordance with the amount of incident X-rays. The grid is disposed on a surface of the scintillator array on the X-ray incident side and includes an X-ray shielding plate that absorbs scattering X-rays. The grid is also called a collimator (one-dimensional collimator or two-dimensional collimator). The light sensor array has a function to perform conversion into an electric signal in accordance with the quantity of light from each scintillator and includes a light sensor such as a photodiode. The X-ray detector 112 may be a direct conversion detector including a semiconductor element configured to convert an incident X-ray into an electric signal.

The rotation frame 113 is an annular frame that oppositely supports the X-ray tube 111 and the X-ray detector 112 and rotates the X-ray tube 111 and the X-ray detector 112 through the control device 115. For example, the rotation frame 113 is a cast metal made of aluminum. The rotation frame 113 may further support the X-ray high-voltage device 114, the wedge 116, the collimator 117, the DAS 118, and the like in addition to the X-ray tube 111 and the X-ray detector 112. In addition, the rotation frame 113 may further support various kinds of components (not illustrated) in FIG. 1. Hereinafter, the rotation frame 113 and any part that rotates together with the rotation frame 113 in the gantry 110 are also referred to as a rotation unit.

The X-ray high-voltage device 114 includes a high-voltage generation device including electric circuitry such as a transformer and a rectifier and configured to generate high voltage to be applied to the X-ray tube 111, and an X-ray control device configured to control output voltage in accordance with X-rays generated by the X-ray tube 111. The high-voltage generation device may be of a transformer scheme or an inverter scheme. The X-ray high-voltage device 114 may be provided to the rotation frame 113 or a fixation frame (not illustrated).

The control device 115 includes processing circuitry including a central processing unit (CPU) and the like, and a drive mechanism such as a motor or an actuator. The control device 115 receives an input signal from an input interface 143 and controls operation of the gantry 110 and the bed 130. For example, the control device 115 controls rotation of the rotation frame 113, tilt of the gantry 110, and operation of the bed 130. For example, as control to tilt the gantry 110, the control device 115 rotates the rotation frame 113 about an axis parallel to the X-axis direction based on input tilt angle information. The control device 115 may be provided to the gantry 110 or the console 140.

The wedge 116 is an X-ray filter for adjusting the amount of X-rays emitted from the X-ray tube 111. Specifically, the wedge 116 is an X-ray filter that attenuates X-rays emitted from the X-ray tube 111 to the subject P1 so that the X-rays have predetermined distribution. For example, the wedge 116 is a wedge filter or a bow-tie filter and produced by fabricating aluminum or the like to have a predetermined target angle and a predetermined thickness.

The collimator 117 is a lead plate or the like for narrowing the irradiation range of X-rays having transmitted through the wedge 116 and is formed as a slit by combining a plurality of lead plates or the like. The collimator 117 is also called an X-ray aperture. In FIG. 1, the wedge 116 is disposed between the X-ray tube 111 and the collimator 117, but the collimator 117 may be disposed between the X-ray tube 111 and the wedge 116. In this case, the wedge 116 transmits and attenuates X-rays emitted from the X-ray tube 111 and having an irradiation range restricted by the collimator 117.

The DAS 118 acquires a signal of an X-ray detected by each detection element included in the X-ray detector 112. For example, the DAS 118 includes an amplifier configured to perform amplification processing on an electric signal output from each detection element, and an A/D converter configured to convert the electric signal into a digital signal, and generates detection data. The DAS 118 is achieved by, for example, a processor.

The data generated by the DAS 118 is transmitted from a transmitter including a light-emitting diode (LED) and provided to the rotation frame 113 to a receiver including a photodiode and provided to a non-rotating part (for example, the fixation frame; omitted in FIG. 1) of the gantry 110, through optical communication, and is forwarded to the console 140. The non-rotating part is, for example, the fixation frame rotatably supporting the rotation frame 113. The method of data transmission from the rotation frame 113 to the non-rotating part of the gantry 110 is not limited to optical communication but may employ any non-contact data transmission scheme or any contact data transmission scheme.

The bed 130 is an apparatus on which the subject P1 as a scanning target is placed and moved, and includes a base 131, a couch drive device 132, the couchtop 133, and a support frame 134. The base 131 is a housing movably supporting the support frame 134 in the vertical direction. The couch drive device 132 is a drive mechanism configured to move, in the long axis direction of the couchtop 133, the couchtop 133 on which the subject P1 is placed, and includes a motor, an actuator, and the like. The couchtop 133 provided on the upper surface of the support frame 134 is a plate on which the subject P1 is placed. The couch drive device 132 may move, in addition to the couchtop 133, the support frame 134 in the long axis direction of the couchtop 133.

The console 140 includes a memory 141, a display 142, the input interface 143, and processing circuitry 144. In the following description, the console 140 is separated from the gantry 110, but the console 140 or some components of the console 140 may be included in the gantry 110.

The memory 141 is achieved by a semiconductor memory element such as a random access memory (RAM) or a flash memory, a hard disk, an optical disk, or the like. For example, the memory 141 stores various kinds of data acquired through execution of scanning on the subject P1. In addition, for example, the memory 141 stores a computer program for circuitry included in the X-ray CT system 10 to achieve its function. The memory 141 may be achieved by servers (cloud) connected with the X-ray CT system 10 through a network.

The display 142 displays various kinds of information. For example, the display 142 displays a display CT image generated by the processing circuitry 144 and displays an image indicating a result of material decomposition. For example, the display 142 also displays a graphical user interface (GUI) for receiving various operations from a user. For example, the display 142 is a liquid crystal display or a cathode ray tube (CRT) display. The display 142 may be a desktop display, a tablet terminal capable of performing wireless communication with the console 140, or the like.

The input interface 143 receives various input operations from the user, converts such a received input operation into an electric signal, and outputs the electric signal to the processing circuitry 144. For example, the input interface 143 receives a reconstruction condition on reconstruction of CT image data, an image processing condition on generation of a display CT image from CT image data, and the like from the user. For example, the input interface 143 is achieved by a mouse, a keyboard, a truck ball, a switch, a button, a joystick, a touch pad on which an input operation is performed through touch on an operation surface, a touch screen as integration of a display screen and a touch pad, non-contact input circuitry using an optical sensor, voice input circuitry, or the like. The input interface 143 may be provided to the gantry 110. The input interface 143 may be achieved by a tablet terminal or the like capable of performing wireless communication with the console 140. The input interface 143 is not limited to a configuration including a physical operation component such as a mouse or a keyboard. Examples of the input interface 143 include electric signal processing circuitry that receives an electric signal corresponding to an input operation from an external input instrument provided separately from the console 140 and outputs the electric signal to the processing circuitry 144.

The processing circuitry 144 controls operation of the entire X-ray CT system 10 by executing a scanning function 144a, a processing function 144b, and a control function 144c. The scanning function 144a is an exemplary scanning unit. The processing function 144b is an exemplary processing unit.

For example, the processing circuitry 144 executes scanning on the subject P1 by reading a computer program corresponding to the scanning function 144a from the memory 141 and executing the computer program. For example, the scanning function 144a supplies high voltage to the X-ray tube 111 by controlling the X-ray high-voltage device 114. Accordingly, the X-ray tube 111 generates X-rays to be emitted to the subject P1. The scanning function 144a moves the subject P1 into an image capturing port of the gantry 110 by controlling the couch drive device 132. The scanning function 144a controls distribution of X-rays to be emitted to the subject P1 by adjusting the position of the wedge 116 and the opening degree and position of the collimator 117. The scanning function 144a rotates the rotation unit by controlling the control device 115. While scanning is executed by the scanning function 144a, the DAS 118 acquires an X-ray signal from each detection element of the X-ray detector 112 and generates detection data. The scanning function 144a provides preprocessing to the detection data output from the DAS 118. For example, the scanning function 144a provides preprocessing such as logarithmic conversion processing, offset correction processing, inter-channel sensitivity correction processing, or beam hardening correction to the detection data output from the DAS 118. The data provided with the preprocessing is also referred to as raw data. The detection data yet to be provided with the preprocessing and the raw data provided with the preprocessing are also collectively referred to as projection data.

The processing circuitry 144 generates image data based on the projection data provided with the preprocessing by reading a computer program corresponding to the processing function 144b from the memory 141 and executing the computer program. For example, the processing function 144b generates CT image data (volume data) by performing, on the projection data, reconstruction processing using a filter correction back projection method, an iterative approximation reconstruction method, an adaptive iterative approximation reconstruction method, or the like. Alternatively, the processing function 144b may generate CT image data by performing reconstruction processing by artificial intelligence (AI). For example, the processing function 144b generates CT image data by a deep learning reconstruction (DLR) method. In addition, the processing function 144b performs material decomposition among a plurality of reference materials based on the projection data. The processing function 144b may perform material decomposition based on data yet to be provided with the reconstruction processing (projection data) or based on data provided with the reconstruction processing (CT image data). Decomposition processing by the processing function 144b will be described later.

The processing circuitry 144 controls display on the display 142 by reading a computer program corresponding to the control function 144c from the memory 141 and executing the computer program. For example, the control function 144c converts the CT image data generated by the processing function 144b into a display CT image (such as cross-sectional image data of an optional section or three-dimensional image data) by a well-known method based on an input operation received from the user through the input interface 143 or the like. Then, the control function 144c causes the display 142 to display the converted display CT image. In addition, for example, the control function 144c causes the display 142 to display an image indicating a result of material decomposition by the processing function 144b. The control function 144c transmits various kinds of data through a network. For example, the control function 144c transmits the CT image data generated by the processing function 144b and the image indicating a result of material decomposition to an image storage (not illustrated) and stores the CT image data and the image in the image storage.

In the X-ray CT system 10 illustrated in FIG. 1, each processing function is stored in the memory 141 in the form of a computer-executable program. The processing circuitry 144 is a processor configured to read a computer program from the memory 141 and execute the computer program to achieve a function corresponding to the computer program. In other words, the processing circuitry 144 having read a computer program has a function corresponding to the read computer program.

The scanning function 144a, the processing function 144b, and the control function 144c are achieved by the single processing circuitry 144 in the above description with reference to FIG. 1, but the processing circuitry 144 may be configured as a combination of a plurality of independent processors, and each processor may execute a computer program to achieve the corresponding function. The processing functions of the processing circuitry 144 may be distributed or integrated to one or a plurality of processing circuits as appropriate.

Alternatively, the processing circuitry 144 may achieve a function by using a processor of an external apparatus connected through a network. For example, the processing circuitry 144 achieves each function illustrated in FIG. 1 by reading and executing the computer program corresponding to the function from the memory 141 and by using, as calculation resources, servers (cloud) connected with the X-ray CT system 10 through a network.

The exemplary configuration of the X-ray CT system 10 is described above. The following describes processing performed by the X-ray CT system 10 in detail.

Figure 2:
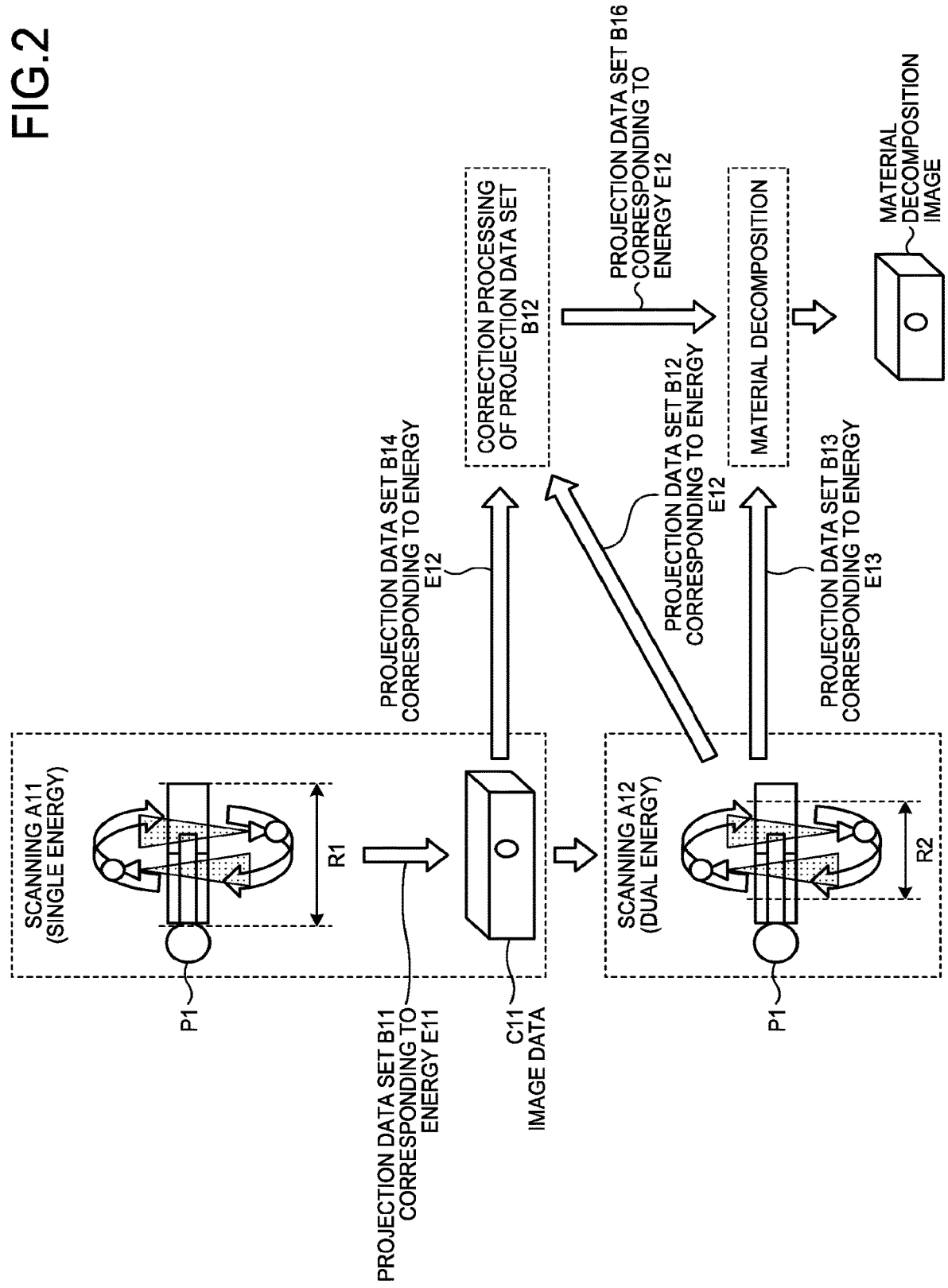
FIG. 2 is a diagram illustrating exemplary processing at the X-ray CT system according to the first embodiment.

The processing performed by the X-ray CT system 10 will be first described below with reference to FIG. 2. FIG. 2 illustrates a case in which Scanning A12 of a kV switching scheme is executed and material decomposition between two kinds of reference materials is performed. FIG. 2 is a diagram illustrating exemplary processing at the X-ray CT system 10 according to the first embodiment.

As illustrated in FIG. 2, the scanning function 144a first executes Scanning A11. Specifically, the scanning function 144a acquires projection data for each of a plurality of irradiation directions (views) by irradiating a range R1 extending in the body axis direction of the subject P1 with X-rays of Energy E11 while rotating the focal position of the X-rays around the subject P1 as illustrated in FIG. 2. Hereinafter, a plurality of pieces of projection data is also referred to as a projection data set.

Accordingly, the scanning function 144a acquires Projection data set B11 corresponding to Energy E11 by irradiating the range R1 with X-rays. For example, the scanning function 144a acquires Projection data set B11 by executing conventional scanning, helical scanning, step-and-shoot scanning, or the like. The processing function 144b reconstructs three-dimensional Image data C11 based on Projection data set B11 acquired by Scanning A11.

Scanning A11 is exemplary first scanning. The range R1 is an exemplary first range or first region. Energy E11 is an exemplary first X-ray energy. Projection data set B11 is an exemplary first projection data set or first subject data set. Image data C11 is an exemplary first image data.

Subsequently, the control function 144c generates a reference image by executing rendering processing on Image data C11 and causes the generated reference image to display the display 142. An example of the rendering processing is processing of generating a two-dimensional image of an optional section from Image data C11 by multi planar reconstruction (MPR). Another exemplary of the rendering processing is processing of generating a two-dimensional image on which three-dimensional information is reflected from Image data C11 by volume rendering processing or maximum intensity projection (MIP). In addition, the control function 144c sets a range R2 as the scanning range of Scanning A12 by receiving an input operation from a user referring to the reference image. Scanning A12 is exemplary second scanning. The range R2 is an exemplary second range or second region.

In other words, Scanning A11 is positioning image capturing for setting the range R2, and Image data C11 is positioning image data used to set the range R2. Thus, the range R1 of Scanning A11 is preferably set to be a relatively wide range including an organ or the like as a diagnosis target. The range R2 is set in the range R1 and thus typically smaller than the range R1 as illustrated in FIG. 2. In other words, the range R2 is included in the range R1. The positioning image data is also called scano-image data, scanogram, or scout image data. Image data C11 as three-dimensional scanogram is also referred to as 3D scanogram.

Subsequently, the scanning function 144a executes Scanning A1t in the range R2 set to the reference image. Specifically, the scanning function 144a executes Scanning A12 by changing the energy of X-rays emitted from the X-ray tube 111 to the subject P1 between Energy E12 and Energy E13 for each of one or a plurality of views. Accordingly, the scanning function 144a acquires Projection data set B12 corresponding to Energy E12 and Projection data set B13 corresponding to Energy E13.

Energy E12 is exemplary second X-ray energy. Projection data set B12 is an exemplary second projection data set or second subject data set. Energy E13 is exemplary third X-ray energy. Projection data set B13 is an exemplary third projection data set or third subject data set. Energy E12 is lower than Energy E13. Energy E11 may be different from Energy E12 and Energy E13 or equal to any of Energy E12 and Energy E13.

Subsequently, the processing function 144b generates Projection data set B14 corresponding to Energy E12 based on Projection data set B11. In addition, the processing function 144b generates Projection data set B16 corresponding to Energy E12 by correcting Projection data set B12 based on Projection data set B14. Accordingly, the processing function 144b generates Projection data set B16 based on Projection data set B12 and Projection data set B14. Projection data set B14 is an exemplary fourth projection data set, and Projection data set B16 is an exemplary sixth projection data set or fourth subject data set. The generation processing of Projection data set B14 and Projection data set B16 will be described later.

Then, the processing function 144b executes material decomposition between two kinds of reference materials based on Projection data set B16 corresponding to Energy E11 and Projection data set B13 corresponding to Energy E13 and generates a material decomposition image.

For example, the processing function 144b separates two reference materials in the range R2 by using Projection data set B16 and Projection data set B13. Specifically, the processing function 144b determines distribution of the linear attenuation coefficient for each of Projection data set B16 and Projection data set B13 and solves a system of equations in Expression (1) below for each position (pixel) of the linear attenuation coefficient, thereby calculating the mixture amount or mixture ratio of the two reference materials at the position.

$$\left.\begin{array}{l}\mu(E1) = \mu_\alpha(E1)c_\alpha + \mu_\beta(E1)c_\beta \\ \mu(E2) = \mu_\alpha(E2)c_\alpha + \mu_\beta(E2)c_\beta\end{array}\right\} \quad (1)$$

In the expression, "$\mu(E1)$" represents the linear attenuation coefficient of each position at single color X-ray energy "E1", and "$\mu(E2)$" represents the linear attenuation coefficient of each position at single color X-ray energy "E2". In addition, "$\mu_\alpha(E)$" represents the linear attenuation coefficient of Reference material $\alpha$, and "$\mu_\beta(E)$" represents the linear attenuation coefficient of Reference material $\beta$. In addition, "$c_\alpha$" represents the mixture amount of Reference material $\alpha$, and "$c_\beta$" represents the mixture amount of Reference material $\beta$. The linear attenuation coefficient for the energy of each reference material is known. For example, the processing function 144b substitutes Energy E11 into "E1" and Energy E12 into "E2" and solves the system of equations of Expression (1), thereby performing material decomposition between the two kinds of reference materials "$\alpha$ and $\beta$".

Then, the processing function 144b generates an image illustrating a result of the material decomposition. For example, the processing function 144b generates a material decomposition image for each reference material. For example, the processing function 144b generates a material decomposition image in which Reference material $\alpha$ illustrates in an emphasized manner, and a material decomposition image in which Reference material $\beta$ is illustrated in an emphasized manner. In addition, the processing function 144b may generate various kinds of images at predetermined energy such as a virtual single-color X-ray image (also referred to as a monochromatic image), a density image, and an effective atomic number image by performing weighted calculation processing based on the mixture ratio of each reference material by using a plurality of material decomposition images generated for the respective reference materials. The control function 144c causes the display 142 to display an image illustrating these material decomposition results.

In the above description, material decomposition is performed before the reconstruction processing is provided, but the processing function 144b may perform material decomposition after the reconstruction processing is provided. Specifically, the processing function 144b may perform material decomposition by solving the system of equations of Expression (1) for each pixel of Projection data set B16 and Projection data set B13 or by solving the system of equations of Expression (1) for each pixel of a CT image data based on Projection data set B16 and a CT image data based on Projection data set B13.

In Expression (1) described above, "μ" represents the linear attenuation coefficient, and "c" represents the mixture amount, but the embodiment is not limited thereto. For example, the processing function 144b may solve Expression (1) with "μ" as the mass attenuation coefficient and "c" as the density for each material.

Figure 3:
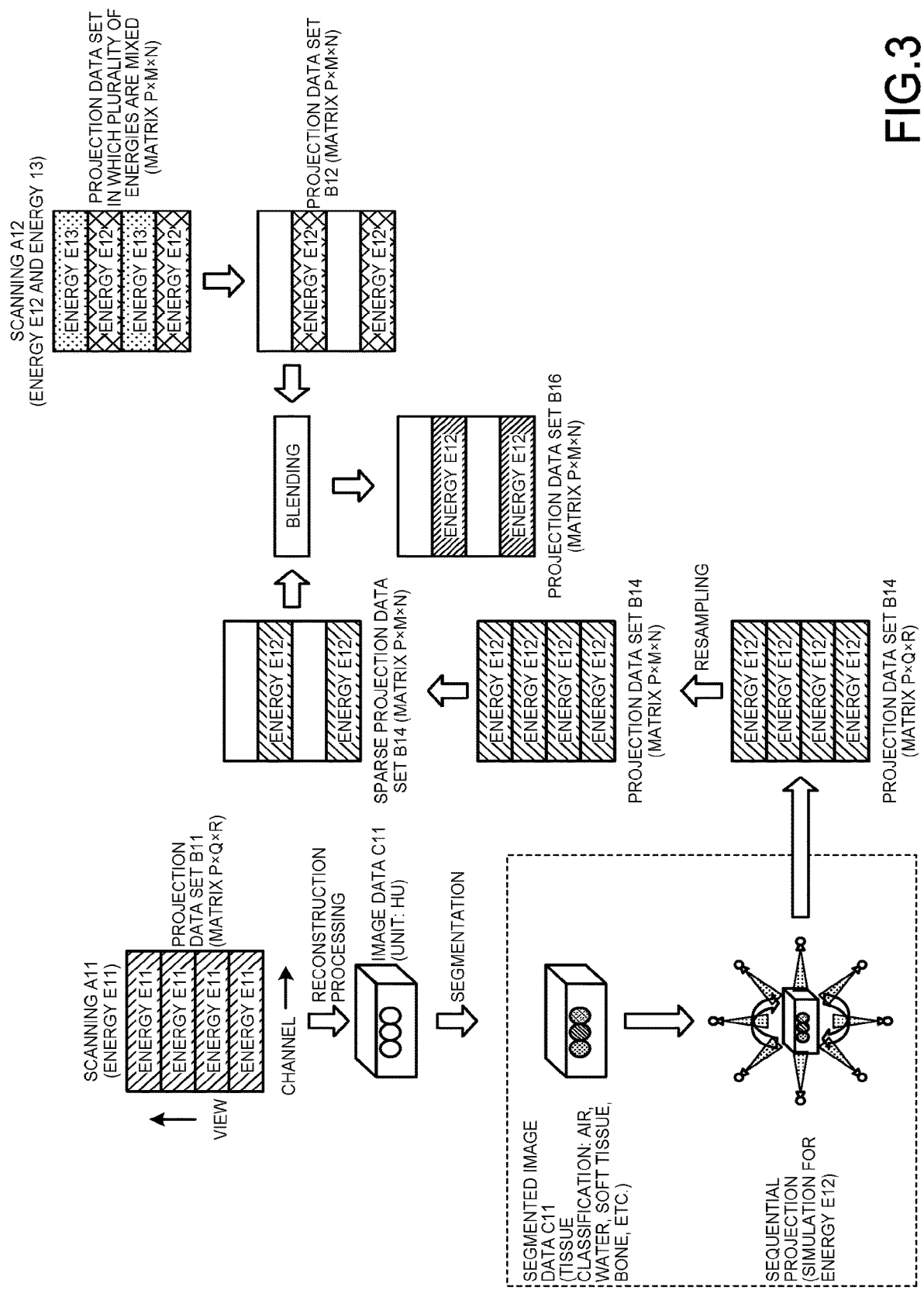
FIG. 3 is a diagram for description of projection data set correction processing according to the first embodiment.

The following describes the generation processing of Projection data set B14 and Projection data set B16 in more detail with reference to FIG. 3. Specifically, as illustrated in FIG. 3, the X-ray CT system 10 generates Projection data set B14 from Projection data set B11 acquired by Scanning A11, and generates Projection data set B16 by correcting, by using Projection data set B14, Projection data set B12 acquired by Scanning A12. Thus, FIG. 3 is a diagram for description of the correction processing of Projection data set B12 according to the first embodiment.

More specifically, the scanning function 144a first executes Scanning A11 and acquires Projection data set B11 corresponding to Energy E11. Projection data set B11 can be expressed as data having axes in a channel direction and a view direction as illustrated in FIG. 3. Scanning A11 is executed by using X-rays of single energy (Energy E11), and thus Projection data set B11 is data of Energy E11 for any view. Thus, Scanning A11 is single-energy scanning using X-rays of Energy E11.

Although not illustrated in FIG. 3, Projection data set B11 is three-dimensional data having the body axis direction of the subject P1 (the Z-axis direction). For example, Projection data set B11 has matrix sizes of "P" in the channel direction, "Q" in the view direction, and "R" in the body axis direction.

Subsequently, the processing function 144b generates three-dimensional Image data C11 by executing the reconstruction processing based on Projection data set B11. Image data C11 is three-dimensional data indicating distribution of a CT value (unit: HU).

Subsequently, the processing function 144b segments Image data C11 in accordance with the CT value. Specifically, the processing function 144b performs tissue classification of each pixel in Image data C11 into air, water, soft tissue, bone, and the like in accordance with the CT value. The CT value is proportional to an X-ray absorption coefficient. Thus, the processing function 144b segments Image data C11 in accordance with the X-ray absorption coefficient.

Figure 4A:
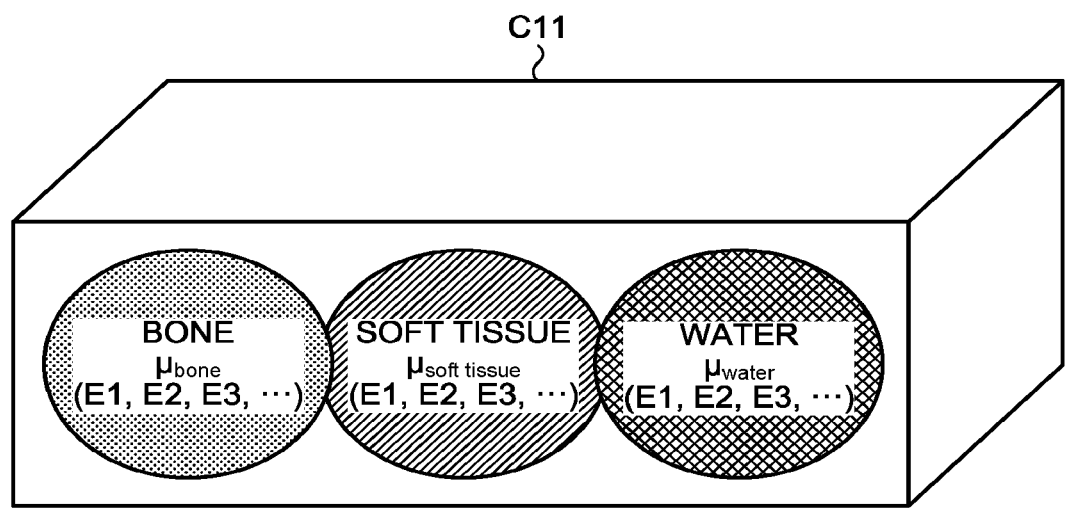
FIG. 4A is a diagram for description of segmentation according to the first embodiment.
Figure 4B:
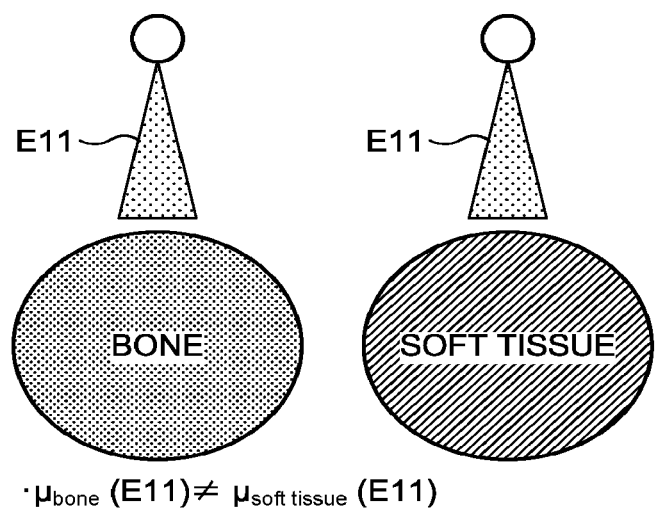
FIG. 4B is a diagram for description of the segmentation according to the first embodiment.
Figure 4C:
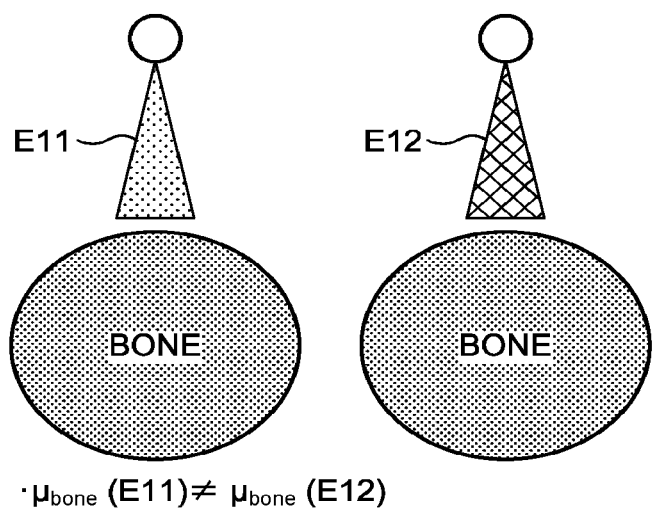
FIG. 4C is a diagram for description of the segmentation according to the first embodiment.

The following describes the segmentation of Image data C11 by the processing function 144b in more detail with reference to FIGS. 4A, 4B, and 4C. FIGS. 4A, 4B, and 4C are diagrams for description of the segmentation according to the first embodiment.

FIG. 4A illustrates the segmented Image data C11. For example, the processing function 144b classifies each pixel in Image data C11 into any of tissues such as air, water, soft tissue, and bone. Different tissues indicate different attenuation coefficients, respectively. For example, as illustrated in FIG. 4B, the attenuation coefficient is different between a bone and a soft tissue for irradiation with X-rays of the same Energy E11. Thus, "μbone(E11)≠μsoft tissue(E11)" holds. Different X-ray energies indicate different attenuation coefficients, respectively. For example, as illustrated in FIG. 4C, the attenuation coefficient is different between X-rays of Energy E11 and X-rays of Energy E11 for irradiation of an identical tissue "bone" with X-rays. Thus, "μbone(E11) ≠ μbone(E12)" holds. In the above description, the segmentation is performed for each pixel, but the processing function 144b may perform segmentation for each pixel group as a bundle of a plurality of pixels.

Subsequently, the processing function 144b generates Projection data set B14 by sequentially projecting Image data C11 in accordance with Energy E12. Specifically, the attenuation coefficient for the energy of each tissue is known, and thus the processing function 144b can simulate a projection data set acquired at Energy E11 by sequentially projecting, in accordance with Energy E12, Image data C11 segmented for each tissue and can generate Projection data set B14. Accordingly, Projection data set B11 is a projection data set actually acquired by Scanning A11, whereas Projection data set B14 is a simulated projection data set. For example, the processing function 144b generates Projection data set B14 by calculating attenuation of an X-ray of Energy E12 that occurs when the X-ray transmits through various tissues.

Subsequently, the processing function 144b performs resampling of Projection data set B14. Specifically, Projection data set B14 generated through sequentially projection has a "P×Q×R" matrix that is same as that of Projection data set B11, but the matrix of Projection data set B14 is different from the matrix of the projection data set acquired by Scanning A12 in some cases. Thus, the processing function 144b performs resampling of Projection data set B14 so that the dimensions of the matrix of Projection data set B14 become equal to the dimensions of the matrix of the projection data set acquired by Scanning A12.

For example, the projection data set acquired by Scanning A12 has a "P×M×N" matrix. Specifically, the matrix size in the channel direction typically does not change, and thus the projection data set acquired by Scanning A12 has the matrix size "P" in the channel direction like Projection data set B14. However, the matrix sizes in the view direction and the body axis direction can change for each scanning. For example, Projection data set B14 has the matrix size "Q" in the view direction and the matrix size "R" in the body axis direction, whereas the projection data set acquired by Scanning A12 has the matrix size "M" in the view direction and the matrix size "N" in the body axis direction. Thus, the processing function 144b performs resampling so that the matrix of Projection data set B14 has a size of "P×M×N".

Subsequently, the processing function 144b fabricates Projection data set B14 into a sparse state. Specifically, the processing function 144b generates sparse Projection data set B14 by fabricating Projection data set B14 generated through sequential projection into a sparse state similar to that of Projection data set B12 corresponding to Energy E12.

Specifically, the projection data set acquired by Scanning A12 is a projection data set in which a plurality of energies (Energy E12 and Energy E13) are mixed as illustrated in FIG. 3. Projection data set B12 separated from the projection data set acquired by Scanning A12 is sparse data in which data corresponding to the view of Energy E13 is missing. Thus, the processing function 144b fabricates Projection data set B14 into a sparse state similar to that of Projection data set B12.

The processing process illustrated in FIG. 3 is merely exemplary and may be changed as appropriate. For example, the processing function 144b may first fabricate Projection data set B14 into a sparse state and then perform resampling from "P×Q×R" to "P×M×N". For example, the processing function 144*b* may perform resampling of Projection data set B11 and then reconstruct Image data C11. For example, the processing function 144*b* may perform resampling of Image data C11 and then perform segmentation. For example, the processing function 144*b* may perform resampling of the segmented Image data C11 and then perform sequential projection. In the description with reference to FIG. 3, non-sparse full data is generated through sequential projection and then fabricated to generate sparse data, but the processing function 144*b* may generate sparse data through sequential projection.

As described above, the processing function 144*b* generates Projection data set B14 by sequentially projecting Image data C11 and performs various kinds of fabrication on Projection data set B14. For example, the processing function 144*b* equalizes the matrix dimensions of Projection data set B14 and Projection data set B12 and fabricates Projection data set B14 into a sparse state similar to that of Projection data set B12. In other words, the processing function 144*b* fabricates Projection data set B14 into a data format same as that of Projection data set B12.

Subsequently, the processing function 144*b* generates Projection data set B16 by blending Projection data set B14 and Projection data set B12. For example, the processing function 144*b* generates Projection data set B16 by positioning Projection data set B14 and Projection data set B12 and performing weighted summation of Projection data set B14 and Projection data set B12 at a predetermined ratio. In other words, the processing function 144*b* generates Projection data set B16 by correcting Projection data set B12 with Projection data set B14.

Alternatively, the processing function 144*b* may perform correction of Projection data set B12 based on Projection data set B14 by AI. For example, the processing function 144*b* generates in advance a learned model M1 functionalized to receive inputting of two projection data sets acquired from an identical target and output a high-quality projection data set, and stores the generated learned model M1 in the memory 141. Then, when Scanning A11 and Scanning A12 are executed, the processing function 144*b* generates Projection data set B16 by inputting Projection data set B14 and Projection data set B12 to the learned model M1 read from the memory 141.

The following describes exemplary generation processing of the learned model M1. First, the processing function 144*b* acquires, as learning data, a group of projection data sets acquired from an identical target. The group of Projection data set B21, Projection data set B22, and Projection data set B23 will be described below as exemplary learning data. For example, Projection data set B21, Projection data set B22, and Projection data set B23 are acquired by performing three times of scanning on the subject P1, a subject P2 different from the subject P1, a phantom as a replica of a human body, or the like. Projection data set B23 is high-quality projection data set acquired by using X-rays of a higher radiation dose than that for Projection data set B21 and Projection data set B22. Projection data set B21, Projection data set B22, and Projection data set B23 may be acquired in the X-ray CT system 10 or another system.

For example, the processing function 144*b* generates the learned model M1 by executing machine learning with Projection data set B21 and Projection data set B22 as input side data and with high-quality Projection data set B23 as output side data.

The learned model M1 can be configured as, for example, a neural network. The neural network is a network having a structure in which adjacent layers arranged in a layered structure are connected with each other, and through which information propagates from an input layer side to an output layer side. For example, the processing function 144*b* generates the learned model M1 by executing deep learning on a multi-layer neural network by using the above-described learning data. The multi-layer neural network is constituted by, for example, an input layer, a plurality of intermediate layers (hidden layers), and an output layer.

For example, the processing function 144*b* inputs Projection data set B21 and Projection data set B22 as input side data into a neural network. In the neural network, information propagates through connection of adjacent layers in one direction from the input layer side to the output layer side, and a projection data set estimated as Projection data set B23 is output from the output layer.

For example, in the neural network, processing of positioning Projection data set B21 and Projection data set B22, determining weights of Projection data set B21 and Projection data set B22, and blending Projection data set B21 and Projection data set B22 is performed. The weights of Projection data set B21 and Projection data set B22 may be determined for each pixel. Then, a projection data set estimated as high-quality Projection data set B23 is output from the output layer of the neural network. A neural network in which information propagates in one direction from the input layer side to the output layer side is also called a convolutional neural network (CNN).

The processing function 144*b* generates the learned model M1 by adjusting parameters of the neural network so that the neural network can output a preferable result when input side data is input. For example, the processing function 144*b* adjusts parameters of the neural network by using a function (error function) indicating the distance between projection data sets.

For example, the processing function 144*b* calculates an error function indicating the distance between Projection data set B23 and a projection data set estimated by the neural network. Then, the processing function 144*b* adjusts parameters of the neural network so that the calculated error function becomes at a local minimum. Accordingly, the processing function 144*b* generates the learned model M1 functionalized to receive inputting of two projection data sets acquired from an identical target and output a high-quality projection data set. The processing function 144*b* stores the generated learned model M1 in the memory 141.

The learned model M1 may be functionalized to further perform preprocessing of blending of two input projection data sets. For example, when the matrices of the two input projection data sets are different, the learned model M1 performs resampling of at least one of the two input projection data sets. For example, when one of the two input projection data sets is sparse data, the learned model M1 fabricates the other projection data set into similar sparse data.

Although the learned model M1 is configured as a neural network in the above description, the processing function 144*b* may generate the learned model M1 by a machine learning method other than a neural network. In addition, although the learned model M1 is generated by the processing function 144*b* in the above description, the learned model M1 may be generated by another apparatus.

After having generated Projection data set B16 based on Projection data set B12 and Projection data set B14, the processing function 144*b* executes material decomposition between two kinds of reference materials based on Projection data set B16 corresponding to Energy E12 and Projection data set B13 corresponding to Energy E13.

For example, the processing function 144b first interpolates data of any missing part of each projection data set. Specifically, since Projection data set B16 and Projection data set B13 are both sparse data, the processing function 144b produces full data by interpolating data of any missing part of each projection data set. Examples of the interpolation processing by the processing function 144b include linear interpolation, Lagrange interpolation, and sigmoid. Then, the processing function 144b executes material decomposition based on Projection data set B16 and Projection data set B13 in the state of full data. For example, the processing function 144b can separate a kidney stone from a soft tissue through material decomposition processing.

In addition, the processing function 144b generates an image illustrating a result of the material decomposition. For example, the processing function 144b generates a material decomposition image in which "calcium" is emphasized and a material decomposition image in which "water" is emphasized. The processing function 144b can also generate various kinds of images at predetermined energy such as a monochromatic image, a density image, and an effective atomic number image. The control function 144c causes the display 142 to display an image illustrating a result of the material decomposition.

In FIG. 3, the processing function 144b may perform interpolation processing of any missing part of Projection data set B12 before blending of Projection data set B14 and Projection data set B12. Specifically, the processing function 144b may omit processing of fabricating Projection data set B14 into sparse data and blend Projection data set B14 and Projection data set B12 in the state of full data.

Although the matrix of projection data set acquired by Scanning A11 and the matrix of the projection data set acquired by Scanning A12 are different in the above description with reference to FIG. 3, the scanning function 144a may execute Scanning A11 and Scanning A12 so that the matrices of the projection data sets are same. In this case, the processing function 144b may omit the processing of resampling.

When Energy E11 and Energy E12 are equal, the scanning function 144a may omit the processing of reconstruction, segmentation, and sequential projection. Specifically, when Energy E11 and Energy E12 are equal, the scanning function 144a may correct Projection data set B12 by directly using Projection data set B11 acquired by Scanning A11.

Figure 5:
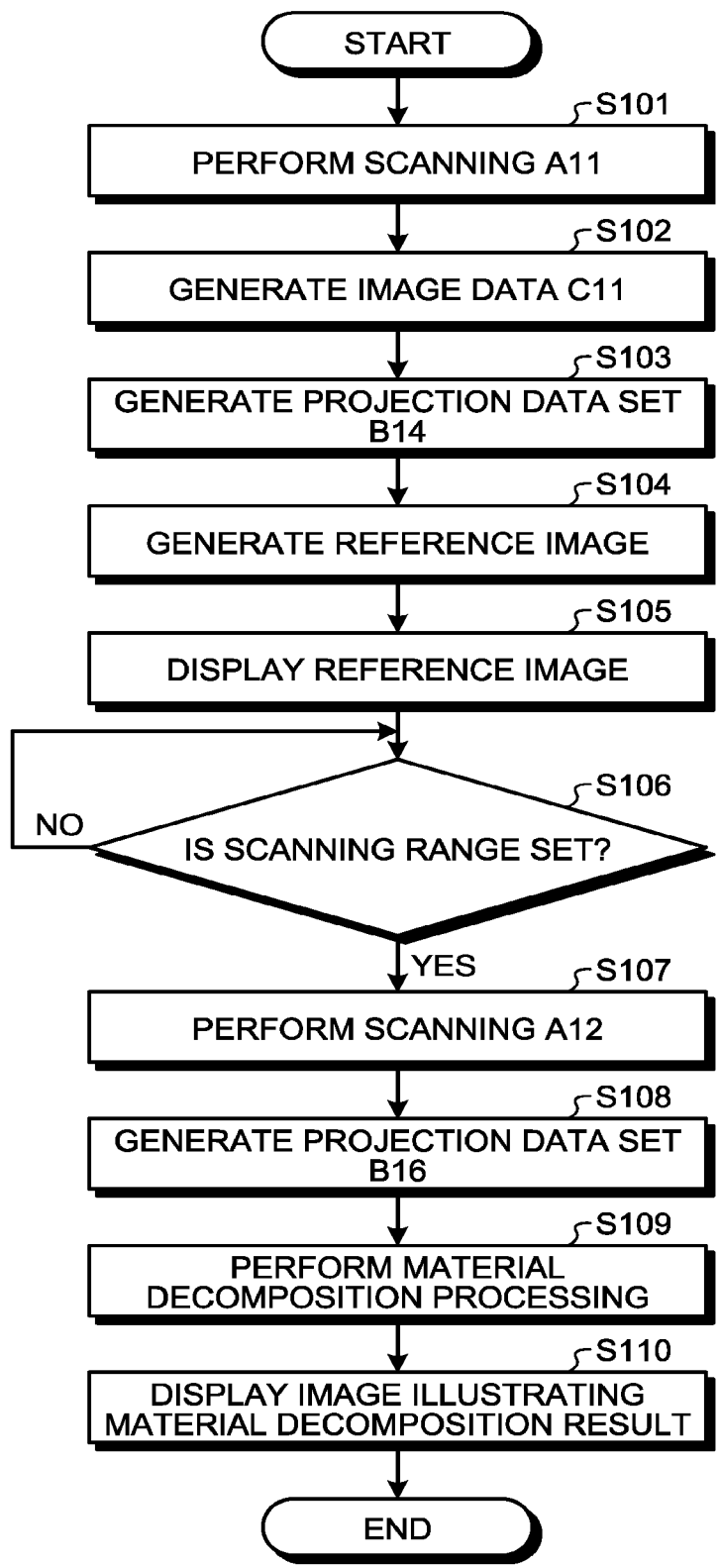
FIG. 5 is a flowchart for description of a series of processes of processing at the X-ray CT system according to the first embodiment.

The following describes an exemplary procedure of processing at the X-ray CT system 10 with reference to FIG. 5. FIG. 5 is a flowchart for description of a series of processes of processing at the X-ray CT system 10 according to the first embodiment.

Steps S101 and S107 correspond to the scanning function 144a. Steps S102, S103, S108, and S109 correspond to the processing function 144b. Steps S104, S105, S106, and S110 correspond to the control function 144c.

First, the processing circuitry 144 executes Scanning A11 by irradiating the range R1 extending in the body axis direction of the subject P1 with X-rays and acquires Projection data set B11 corresponding to Energy E11 (step S101). Subsequently, the processing circuitry 144 generates Image data C11 by executing reconstruction processing of Projection data set B11 (step S102).

Subsequently, the processing circuitry 144 generates Projection data set B14 corresponding to Energy E11 based on Projection data set B11 (step S103). Specifically, the processing circuitry 144 generates Projection data set B14 by segmenting Image data C11 based on Projection data set B11 in accordance with the X-ray absorption coefficient and sequentially projecting the segmented Image data C11 in accordance with Energy E12.

Then, the processing circuitry 144 generates a reference image by performing rendering processing of Image data C11 (step S104) and causes the display 142 to display the generated reference image (step S105). Then, the processing circuitry 144 determines whether the range R2 as the scanning range of Scanning A12 is set by a user referring to the reference image (step S106). When the scanning range is yet to be set, the processing circuitry 144 becomes a standby state (No at step S106).

When the scanning range is set (Yes at step S106), the processing circuitry 144 executes Scanning A12 in the scanning range set to the reference image (step S107). Specifically, the processing circuitry 144 acquires Projection data set B12 corresponding to Energy E12 and Projection data set B13 corresponding to Energy E13 by irradiating the range R2 extending in the body axis direction of the subject P1 with X-rays.

Subsequently, the processing circuitry 144 generates Projection data set B16 corresponding to Energy E11 based on Projection data set B12 and Projection data set B14 (step S108). Subsequently, the processing circuitry 144 performs material decomposition between two kinds of reference materials based on Projection data set B16 corresponding to Energy E11 and Projection data set B13 corresponding to Energy E13 (step S109). Then, the processing circuitry 144 causes the display 142 to display a material decomposition image illustrating a result of the material decomposition (step S110), and ends the processing.

Step S103 and the set of steps S104, S105, S106, and S107 are performed in an optional order and may be performed in parallel.

Although X-ray energy is changed for each view in Scanning A12 in the above description with reference to FIG. 3, the scanning function 144a may change X-ray energy for each set of a plurality of views.

Although Scanning A12 is performed in dual energy (Energy E12 and Energy E13) in the above description with reference to FIG. 3, the scanning function 144a may execute, as Scanning A12, multi-energy scanning using X-rays of three or more kinds of energy. In this case, the processing circuitry 144 can perform material decomposition among three or more kinds of reference materials.

As described above, according to the first embodiment, the scanning function 144a executes Scanning A11 of acquiring Projection data set B11 corresponding to Energy E11 by irradiating the range R1 extending in the body axis direction of the subject P1 with X-rays. The scanning function 144a also executes Scanning A12 of acquiring Projection data set B12 corresponding to Energy E12 and Projection data set B13 corresponding to Energy E13 by irradiating the range R2 extending in the body axis direction of the subject P1 with X-rays. In addition, the processing function 144b generates Projection data set B14 corresponding to Energy E11 based on Projection data set B11. The processing function 144b also performs material decomposition among a plurality of reference materials based on Projection data set B14, Projection data set B12, and Projection data set B13. Thus, the X-ray CT system 10 according to the first embodiment can achieve improved accuracy of material decomposition.

In particular, the quality of Projection data set B12 as low-energy side data is often lower than the quality of Projection data set B13 as high-energy side data. The X-ray CT system 10 can improve the quality of the low-energy side data by correcting Projection data set B12 based on Projection data set B14. Accordingly, the X-ray CT system 10 can achieve improved accuracy of material decomposition based on the low-energy side data and the high-energy side data.

The processing function 144b generates Projection data set B14 by generating Image data C11 based on Projection data set B11, segmenting Image data C11 in accordance with the X-ray absorption coefficient, sequentially projecting the segmented Image data C11 in accordance with Energy E12. At least part of noise contained in Projection data set B11 is removed through the processing of reconstruction and sequential projection. Accordingly, Projection data set B14 becomes data having noise less than that of Projection data set B11. Thus, the X-ray CT system 10 can accurately correct Projection data set B12 by generating Projection data set B14 as compared to a case in which Projection data set B12 is corrected by directly using Projection data set B11.

Scanning A11 is positioning scanning for executing Scanning A12 and included in a typical processing process. Thus, execution of Scanning A11 does not complicate the processing process nor increase the amount of radiation exposure of the subject P1.

The X-ray CT system 10 uses a result of Scanning A11 in the positioning for Scanning A12 and also in the processing of material decomposition. Thus, the X-ray CT system 10 can provide more meaningfulness to radiation exposure of the subject P1 through Scanning A11.

The first embodiment is described above, but various kinds of different forms other than the above-described embodiment are possible.

For example, in the above-described embodiment, among Projection data set B12 and Projection data set B13 acquired by Scanning A12, only Projection data set B12 is corrected based on Projection data set B11 acquired by Scanning A11. However, the embodiment is not limited thereto, and the processing function 144b may correct Projection data set B13 based on Projection data set B11.

For example, the processing function 144b first generates Image data C11 based on Projection data set B11 and segments Image data C11 in accordance with the X-ray absorption coefficient. Subsequently, the processing function 144b generates Projection data set B15 by sequentially projecting the segmented Image data C11 in accordance with Energy E13. Projection data set B15 is an exemplary fifth projection data set.

Subsequently, the processing function 144b generates Projection data set B17 corresponding to Energy E13 based on Projection data set B13 and Projection data set B15. Specifically, the processing function 144b generates Projection data set B17 by correcting Projection data set B13 based on Projection data set B15. For example, the processing function 144b generates Projection data set B17 by inputting Projection data set B13 and Projection data set B15 to the learned model M1. Projection data set B17 is an exemplary seventh projection data set or fourth subject data set. Then, the processing function 144b performs material decomposition based on Projection data set B12 corresponding to Energy E12 and Projection data set B17 corresponding to Energy E13.

The quality of Projection data set B13 as high-energy side data is typically high, but when the physical size of the subject P1 is large, noise is contained in Projection data set B13 in some cases. In addition, artifacts occur to Projection data set B13 in some cases due to various kinds of factors such as an electrical discharging phenomenon that occurs in the X-ray tube 111 and body motion of the subject P1. In such a case, the processing function 144b can correct Projection data set B13 based on Projection data set B11 acquired by Scanning A11.

Alternatively, the processing function 144b may correct both Projection data set B12 and Projection data set B13 based on Projection data set B11 acquired by Scanning A11.

For example, the processing function 144b first generates Image data C11 based on Projection data set B11 and segments Image data C11 in accordance with the X-ray absorption coefficient. Subsequently, the processing function 144b generates Projection data set B14 by sequentially projecting the segmented Image data C11 in accordance with Energy E12. The processing function 144b also generates Projection data set B15 by sequentially projecting the segmented Image data C11 in accordance with Energy E13.

Subsequently, the processing function 144b generates Projection data set B16 corresponding to Energy E12 based on Projection data set B12 and Projection data set B14. For example, the processing function 144b generates Projection data set B16 by inputting Projection data set B12 and Projection data set B14 into the learned model M1. The processing function 144b also generates Projection data set B17 corresponding to Energy E13 based on Projection data set B13 and Projection data set B15. For example, the processing function 144b generates Projection data set B17 by inputting Projection data set B13 and Projection data set B15 into the learned model M1. Then, the processing function 144b performs material decomposition based on Projection data set B16 corresponding to Energy E11 and Projection data set B17 corresponding to Energy E13.

In the above-described embodiment, Projection data set B14 and Projection data set B15 are generated from Projection data set B11 by the processing of reconstruction, segmentation, and sequential projection. However, the embodiment is not limited thereto.

For example, the processing function 144b may generate Projection data set B14 and Projection data set B15 from Projection data set B11 by scaling processing. The scaling processing generates data of different energies based on a property that the transmission amount of an X-ray changes in accordance with the energy of the X-ray. For example, the processing function 144b generates Projection data set B14 corresponding to Energy E12 by approximating the transmission amount of an X-ray in Projection data set B11 to the transmission amount of the X-ray when the energy of the X-ray is Energy E12 through multiplication of Projection data set B11 by a coefficient in accordance with the difference between Energy E11 and Energy E12. For example, the processing function 144b also generates Projection data set B15 corresponding to Energy E13 by approximating the transmission amount of an X-ray in Projection data set B11 to the transmission amount of the X-ray when the energy of the X-ray is Energy E13 through multiplication of Projection data set B11 by a coefficient in accordance with the difference between Energy E11 and Energy E13.

In the above-described embodiment, the range R2 as the scanning range of Scanning A12 is set by a user, but the embodiment is not limited thereto. For example, the control function 144c may automatically set the range R2 by analyzing Image data C11 or a reference image generated based on Image data C11 and extracting an organ or the like as a diagnosis target.

In the above-described embodiment, Scanning A11 is positioning scanning for setting the range R2 as the scanning range of Scanning A12, but the embodiment is not limited thereto. For example, Scanning A11 may be scanning executed on a day different from a day on which Scanning A12 is executed. Scanning A11 may be scanning executed after Scanning A12.

In the above-described embodiment, Scanning A12 of the kV switching scheme is executed to acquire Projection data set B12 and Projection data set B13. However, the embodiment is not limited thereto.

For example, the scanning function 144a may execute, in place of Scanning A12, Scanning A13 of a layered detector scheme (also referred to as a dual layer scheme). In this case, the X-ray CT system 10 includes a layered detector as the X-ray detector 112. For example, the X-ray detector 112 includes a first layer 112a and a second layer 112b and disperses and detects an X-ray emitted from the X-ray tube 111. Then, the scanning function 144a can acquire, by executing Scanning A13, Projection data set B12 based on a result of the detection by the first layer 112a and Projection data set B13 based on a result of the detection by the second layer 112b.

Alternatively, for example, the scanning function 144a may execute Scanning A14 of a dual source scheme in place of Scanning A12 or Scanning A13. In this case, the X-ray CT system 10 includes an X-ray tube 1111 and an X-ray tube 1112 as the X-ray tube 111. The X-ray CT system 10 also includes, as the X-ray detector 112, an X-ray detector 1121 configured to detect an X-ray emitted from the X-ray tube 1111, and an X-ray detector 1122 configured to detect an X-ray emitted from the X-ray tube 1112. Then, the scanning function 144a can acquire, by executing Scanning A14, Projection data set B12 based on a result of the detection by the X-ray detector 1121 and Projection data set B13 based on a result of the detection by the X-ray detector 1122.

Alternatively, for example, the scanning function 144a may execute Scanning A15 of a split scheme in place of Scanning A12, Scanning A13, or Scanning A14. In this case, the X-ray CT system 10 includes, as the wedge 116, a filter configured to divide an X-ray emitted from the X-ray tube 111 into a plurality of X-rays having different energies.

For example, the X-ray CT system 10 includes, as the wedge 116, an X-ray filter 116a and an X-ray filter 116b. The X-ray filter 116a and the X-ray filter 116b have different materials, thicknesses, and the like and divide an X-ray having an identical energy into a plurality of X-rays having different energies. In this case, the scanning function 144a attenuates the energy of an X-ray emitted from the X-ray tube 111 to Energy E12 through the X-ray filter 116a and to Energy E13 through the X-ray filter 116b and executes Scanning A15. More specifically, in a configuration that the X-ray filter 116a and the X-ray filter 116b are arranged in the Z-axis direction (column direction) illustrated in FIG. 1, the scanning function 144a irradiates the X-ray filter 116a and the X-ray filter 116b with X-rays from the X-ray tube 111. Accordingly, the scanning function 144a can acquire Projection data set B12 corresponding to Energy E12 and Projection data set B13 corresponding to Energy E13 by executing Scanning A15 while X-rays of Energy E12 and X-rays of Energy E13 are distributed in the column direction.

For example, the X-ray CT system 10 includes only an X-ray filter 116c as the wedge 116. For example, the scanning function 144a emits X-rays of Energy E13 from the X-ray tube 111, attenuates some X-rays to Energy E12 through the X-ray filter 116c, and executes Scanning A15. More specifically, the scanning function 144a attenuates X-rays in a predetermined range in the column direction from Energy E13 to Energy E12 through the X-ray filter 116b and irradiates the subject P1 with the X-rays. X-rays not subjected to the attenuation through the X-ray filter 116b are incident on the subject P1 at Energy E13. Accordingly, the scanning function 144a can acquire Projection data set B12 corresponding to Energy E12 and Projection data set B13 corresponding to Energy E13 by executing Scanning A15 while X-rays of Energy E11 and X-rays of Energy E13 are distributed in the column direction.

Projection data set B12 and Projection data set B13 acquired by the dual layer scheme, the dual source scheme, or the split scheme are not sparse data, and thus the processing function 144b does not need perform interpolation processing on Projection data set B12 and Projection data set B13 nor fabrication of Projection data set B14 and Projection data set B15 based on Projection data set B11 into sparse data.

In the above-described embodiment, Projection data set B12 and Projection data set B13 are correction targets. Specifically, correction is performed in a projection data region in the above-described embodiment. However, the embodiment is not limited thereto. For example, the processing function 144b may perform correction in an image region.

For example, the processing function 144b reconstructs three-dimensional Image data C11 corresponding to Energy E11 based on Projection data set B11 acquired by Scanning A11. The processing function 144b also reconstructs three-dimensional Image data C12 corresponding to Energy E12 based on Projection data set B12 acquired by Scanning A12. The processing function 144b also reconstructs three-dimensional Image data C13 corresponding to Energy E13 based on Projection data set B13 acquired by Scanning A12. Image data C11 is an exemplary first subject data set. Image data C12 is an exemplary second subject data set. Image data C13 is an exemplary third subject data set.

Subsequently, the processing function 144b corrects at least one of Image data C12 and Image data C13 based on Image data C11. Image data C11 corresponds to an X-ray energy different from those of Image data C12 and Image data C13 but has valuable information on X-ray attenuation and an anatomical structure in the subject P1. Thus, the processing function 144b can improve the quality of reconstruction images such as Image data C12 and Image data C13 based on Image data C11. Then, the processing function 144b executes the processing of material decomposition based on Image data C12 and Image data C13, at least one of which is corrected.

When performing correction in an image region, the processing function 144b may omit the above-described processing of generating Projection data set B14 and Projection data set B15. Specifically, the processing function 144b may omit processing of simulating a projection data set of other energy.

The above-described correction processing in an image region can also be achieved by a machine learning method. For example, the processing function 144b generates in advance a learned model M2 functionalized to receive inputting of image data based on the first scanning and image data based on the second scanning and correct the image data based on the second scanning, and stores the learned model M2 in the memory 141. When Scanning A11 and Scanning A12 are executed, the processing function 144b generates Image data C12' corrected from Image data C12 by inputting Image data C11 based on Scanning A11 and Image data C12 based on Scanning A12 to the learned model M2 read from the memory 141. Then, the processing function 144b executes the processing of material decomposition based on Image data C12' corresponding to Energy E12 and Image data C13 corresponding to Energy E13. Image data C12' is an exemplary fourth subject data set. Specifically, the processing function 144b executes the processing of material decomposition based on: the fourth subject data set obtained based on the first subject data set and the second subject data set; and the third subject data set.

Alternatively, the processing function 144b generates Image data C13' corrected from Image data C13 by inputting Image data C11 based on Scanning A11 and Image data C13 based on Scanning A12 to the learned model M2. Then, the processing function 144b executes the processing of material decomposition based on Image data C12 corresponding to Energy E11 and Image data C13 corresponding to Energy E13'. Image data C13' is an exemplary fourth subject data set. Specifically, the processing function 144b executes the processing of material decomposition based on: the fourth subject data set obtained based on the first subject data set and the third subject data set; and the second subject data set.

Alternatively, the processing function 144b generates, by using the learned model M2, both Image data C12' corrected from Image data C12 and Image data C13' corrected from Image data C13. Then, the processing function 144b executes the processing of material decomposition based on Image data C12 corresponding to Energy E12' and Image data C13 corresponding to Energy E13'. Specifically, the processing function 144b executes the processing of material decomposition based on: the fourth subject data set obtained based on the first subject data set and the second subject data set; and the fourth subject data set obtained based on the first subject data set and the third subject data set.

The learned model M2 may be configured in a manner similar to the learned model M1. For example, the learned model M2 may be configured as a neural network. For example, the processing function 144b generates the learned model M2 by executing deep learning on a multi-layer neural network. The type of a neural network is not particularly limited but may be a convolution neural network (CNN) or any other neural network such as a fully connected neural network or a recurrent neural network (RNN). Alternatively, the processing function 144b may generate the learned model M2 by a machine learning method other than a method using a neural network. The processing function 144b does not need to perform generation processing of the learned model M2 but may acquire and use the learned model M2 generated by another apparatus.

In the above description, at least Projection data set B12 corresponding to Energy E11 and Projection data set B13 corresponding to Energy E13 are acquired in the second scanning. However, the embodiment is not limited thereto. For example, the scanning function 144a may acquire any one of Projection data set B12 and Projection data set B13 in the second scanning. In this case, the processing function 144b can correct any one of Projection data set B12 and Projection data set B13 based on Projection data set B11 and reconstruct high-quality CT image data based on the corrected projection data set. Alternatively, the processing function 144b may correct, based on Image data C11 reconstructed from Projection data set B11, any one of Image data C12 reconstructed from Projection data set B12 and Image data C13 reconstructed from Projection data set B13, thereby improving the quality.

Figure 6:
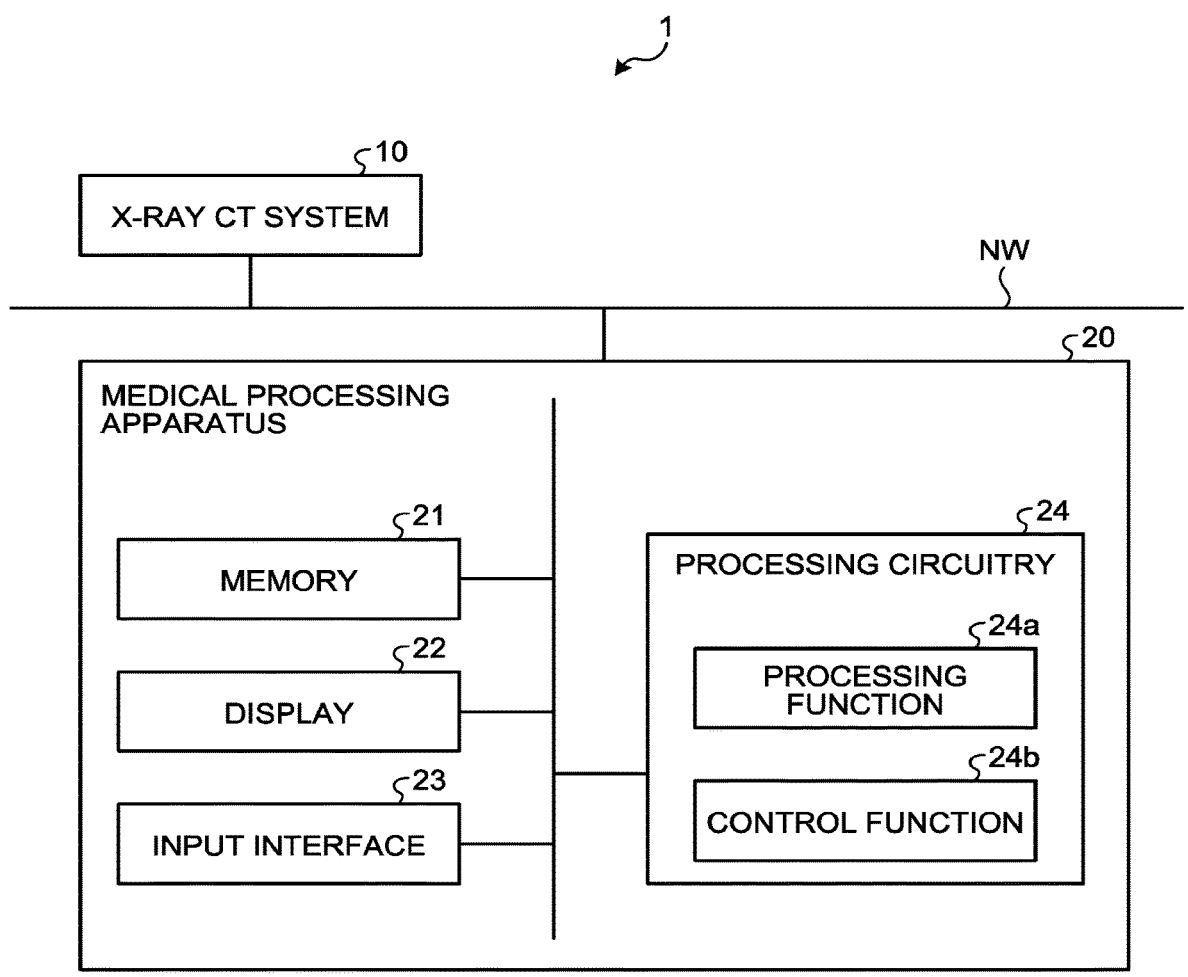
FIG. 6 is a block diagram illustrating an exemplary configuration of a medical information processing system according to a second embodiment.

In the above description, material decomposition is executed by the X-ray CT system 10, but the embodiment is not limited thereto. For example, material decomposition may be executed by another apparatus different from the X-ray CT system 10. This point will be described below with an example of a medical information processing system 1 illustrated in FIG. 6. FIG. 6 is a block diagram illustrating an exemplary configuration of the medical information processing system 1 according to a second embodiment. The medical information processing system 1 includes the X-ray CT system 10 and a medical processing apparatus 20 configured to execute material decomposition.

As illustrated in FIG. 6, the X-ray CT system 10 and the medical processing apparatus 20 are connected with each other through a network NW. The X-ray CT system 10 and the medical processing apparatus 20 may be installed at optional places as long as connection therebetween is possible through the network NW. For example, the medical processing apparatus 20 may be installed at a hospital different from the place of the X-ray CT system 10. Specifically, the network NW may be configured as a local network closed to the hospital or a network through the Internet. Although one X-ray CT system 10 is illustrated in FIG. 6, a plurality of X-ray CT systems 10 may be included in the medical information processing system 1.

The medical processing apparatus 20 is achieved by a computer such as a workstation. For example, as illustrated in FIG. 6, the medical processing apparatus 20 includes a memory 21, a display 22, an input interface 23, and processing circuitry 24.

The memory 21 is achieved by, for example, a semiconductor memory element such as a RAM or a flash memory, a hard disk, or an optical disk. For example, the memory 21 stores various kinds of data transmitted from the X-ray CT system 10. For example, the memory 21 also stores a computer program for circuitry included in the medical processing apparatus 20 to achieve its function. The memory 21 may be achieved by servers (cloud) connected with the medical processing apparatus 20 through the network NW.

The display 22 displays various kinds of information. For example, the display 22 displays an image illustrating a result of material decomposition by the processing circuitry 24, a GUI for receiving various operations from a user, and the like. For example, the display 22 is a liquid crystal display or a CRT display. The display 22 may be a desktop display, a tablet terminal capable of performing wireless communication with the medical processing apparatus 20, or the like.

The input interface 23 receives various input operations from the user, converts such a received input operation into an electric signal, and outputs the electric signal to the processing circuitry 24. For example, the input interface 23 receives a reconstruction condition on reconstruction of CT image data, an image processing condition on generation of a display CT image from CT image data, and the like from the user. For example, the input interface 23 is achieved by a mouse, a keyboard, a truck ball, a switch, a button, a joystick, a touch pad on which an input operation is performed through touch on an operation surface, a touch screen as integration of a display screen and a touch pad, non-contact input circuitry using an optical sensor, voice input circuitry, or the like. The input interface 23 may be achieved by a tablet terminal or the like capable of performing wireless communication with the medical processing apparatus 20. The input interface 23 is not limited to a configuration including a physical operation component such as a mouse or a keyboard. Examples of the input interface 23 included electric signal processing circuitry that receives an electric signal corresponding to an input operation from an external input instrument provided separately from the medical processing apparatus 20 and outputs the electric signal to the processing circuitry 24.

The processing circuitry 24 controls operation of the entire medical processing apparatus 20 by executing a processing function 24a and a control function 24b. The processing function 24a is an exemplary processing unit. Processing by the processing circuitry 24 will be described later.

In the medical processing apparatus 20 illustrated in FIG. 6, each processing function is stored in the memory 21 in the form of a computer-executable program. The processing circuitry 24 is a processor configured to read a computer program from the memory 21 and execute the computer program to achieve a function corresponding to the computer program. In other words, the processing circuitry 24 having read a computer program has a function corresponding to the read computer program.

The processing function 24a and the control function 24b are achieved by the single processing circuitry 24 in the above description with reference to FIG. 6, but the processing circuitry 24 may be configured as a combination of a plurality of independent processors, and each processor may execute a computer program to achieve the corresponding function. The processing functions of the processing circuitry 24 may be distributed or integrated to one or a plurality of processing circuits as appropriate.

Alternatively, the processing circuitry 24 may achieve a function by using a processor of an external apparatus connected through the network NW. For example, the processing circuitry 24 achieves each function illustrated in FIG. 6 by reading and executing a computer program corresponding to each function from the memory 21 and by using, as calculation resources, servers (cloud) connected with the medical processing apparatus 20 through the network NW.

For example, the scanning function 144a in the X-ray CT system 10 first executes Scanning A11 by irradiating the range R1 extending in the body axis direction of the subject P1 with X-rays and acquires Projection data set B11 corresponding to Energy E11. The scanning function 144a also executes Scanning A12 by irradiating the range R2 extending in the body axis direction of the subject P1 with X-rays and acquires Projection data set B12 corresponding to Energy E12 and Projection data set B13 corresponding to Energy E13. The scanning function 144a may execute, in place of Scanning A12 of the kV switching scheme, Scanning A13 of the dual layer scheme, Scanning A14 of the dual source scheme, or Scanning A15 of the split scheme. The control function 144c transmits Projection data set B11, Projection data set B12, and Projection data set B13 to the medical processing apparatus 20 through the network NW.

Subsequently, the processing function 24a of the medical processing apparatus 20 generates at least one of Projection data set B14 corresponding to Energy E12 and Projection data set B15 corresponding to Energy E13 based on Projection data set B11. The processing function 24a performs material decomposition based on at least one of Projection data set B14 and Projection data set B15, Projection data set B12, and Projection data set B13.

For example, the processing function 24a generates Projection data set B16 corresponding to Energy E11 based on Projection data set B12 and Projection data set B14 and performs material decomposition based on Projection data set B16 and Projection data set B13. For example, the processing function 24a also generates Projection data set B17 corresponding to Energy E13 based on Projection data set B13 and Projection data set B15 and performs material decomposition based on Projection data set B12 and Projection data set B17. For example, the processing function 24a also generates Projection data set B16 based on Projection data set B12 and Projection data set B14, generates Projection data set B17 based on Projection data set B13 and Projection data set B15, and performs material decomposition based on Projection data set B16 and Projection data set B17.

The control function 24b causes the display 22 to display an image illustrating a result of the material decomposition by the processing function 24a. Alternatively, the control function 24b transmits the image illustrating a result of the material decomposition to the X-ray CT system 10. In this case, the control function 144c in the X-ray CT system 10 causes the display 142 to display the image illustrating a result of the material decomposition.

The term "processor" used in the above description means, for example, a CPU, a graphics processing unit (GPU), or circuitry such as an application specific integrated circuit (ASIC) or a programmable logic device (for example, a simple programmable logic device (SPLD), a complex programmable logic device (CPLD), or a field programmable gate array (FPGA)). The processor achieves a function by reading and executing a computer program stored in the memory 141 or the memory 21.

In the above description with reference to FIG. 1, the single memory 141 stores a computer program corresponding to each processing function of the processing circuitry 144. In the above description with reference to FIG. 6, the single memory 21 stores a computer program corresponding to each processing function of the processing circuitry 24. However, the embodiment is not limited thereto. For example, a plurality of memories 141 may be disposed in a distributed manner, and the processing circuitry 144 may read a computer program from the corresponding memory 141. Similarly, a plurality of memories 21 may be disposed in a distributed manner, and the processing circuitry 24 may read a computer program from the corresponding memory 21. Instead of being stored in the memory 141 or the memory 21, a computer program may be directly incorporated in a circuit of a processor. In this case, the processor achieves a function by reading and executing the computer program incorporated in the circuit.

Each component of each apparatus according to the above-described embodiments is functionally conceptual and does not necessarily need to be physically configured as illustrated in the drawings. In other words, the specific form of distribution and integration of the apparatus is not limited to those illustrated in the drawings, but the entire or part thereof may be functionally or physically distributed and integrated in arbitrary units in accordance with, for example, various loads and use statuses. Moreover, the entire or an optional part of each processing function performed at each apparatus may be achieved by a CPU and a computer program analyzed and executed by the CPU or may be achieved as wired logic hardware.

Each processing method described in the above-described embodiments can be achieved by executing a processing computer program prepared in advance through a computer such as a personal computer or a workstation. The processing computer program may be distributed through a network such as the Internet. In addition, the processing computer program may be recorded in a computer-readable non-transient recording medium such as a hard disk, a flexible disk (FD), a CD-ROM, an MO, or a DVD, read from the recording medium by a computer, and executed.

According to at least one embodiment described above, it is possible to improve the accuracy of material decomposition.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray CT system comprising processing circuitry configured to:
   execute first scanning of acquiring a first subject data set corresponding to first X-ray energy by irradiating a first region of a subject with X-rays;
   execute, after the first scanning, second scanning of acquiring a second subject data set corresponding to second X-ray energy and a third subject data set corresponding to third X-ray energy different from the second X-ray energy by irradiating a second region included in the first region with X-rays; and
   perform material decomposition among a plurality of reference materials based on: a fourth subject data set obtained based on the first subject data set and one of the second subject data set and the third subject data set; and the other of the second subject data set and the third subject data set.

2. The X-ray CT system according to claim 1, wherein the processing circuitry
   acquires a first projection data set as the first subject data set through execution of the first scanning by irradiating the first region extending in a body axis direction of the subject with X-rays,
   acquires a second projection data set as the second subject data set and acquires a third projection data set as the third subject data set through execution of, after the first scanning, the second scanning by irradiating a second region narrower than the first region extending in the body axis direction with X-rays,
   generates, based on the first projection data set, at least one of a fourth projection data set corresponding to the second X-ray energy and a fifth projection data set corresponding to the third X-ray energy, and
   performs the material decomposition based on: the fourth projection data set and the second projection data set; the fourth subject data set obtained based on one of the fifth projection data set and the third projection data set; and the other of the second projection data set and the third projection data set.

3. The X-ray CT system according to claim 1, wherein the first X-ray energy is different from the second X-ray energy and the third X-ray energy.

4. The X-ray CT system according to claim 2, wherein the second X-ray energy is smaller than the third X-ray energy, and
   the processing circuitry
   generates the fourth projection data set corresponding to the second X-ray energy based on the first projection data set,
   generates a sixth projection data set corresponding to the second X-ray energy based on the second projection data set and the fourth projection data set, and
   performs the material decomposition based on the third projection data set and the sixth projection data set.

5. The X-ray CT system according to claim 2, wherein the processing circuitry
   generates, based on the first projection data set, the fourth projection data set corresponding to the second X-ray energy and the fifth projection data set corresponding to the third X-ray energy,
   generates, based on the second projection data set and the fourth projection data set, a sixth projection data set corresponding to the second X-ray energy,
   generates, based on the third projection data set and the fifth projection data set, a seventh projection data set corresponding to the third X-ray energy, and
   performs the material decomposition based on the sixth projection data set and the seventh projection data set.

6. The X-ray CT system according to claim 4, wherein the processing circuitry generates the fourth projection data set by generating three-dimensional first image data based on the first projection data set, segmenting the first image data in accordance with an X-ray absorption coefficient, and sequentially projecting the segmented first image data in accordance with the second X-ray energy.

7. The X-ray CT system according to claim 5, wherein the processing circuitry generates the fourth projection data set by generating three-dimensional first image data based on the first projection data set, segmenting the first image data in accordance with an X-ray absorption coefficient, and sequentially projecting the segmented first image data in accordance with the second X-ray energy, and generates the fifth projection data set by sequentially projecting the segmented first image data in accordance with the third X-ray energy.

8. The X-ray CT system according to claim 4, wherein the processing circuitry generates the sixth projection data set by inputting the fourth projection data set and the second projection data set to a learned model functionalized to receive inputting of two projection data sets acquired from an identical target and output a high-quality projection data set.

9. The X-ray CT system according to claim 5, wherein the processing circuitry generates the sixth projection data set by inputting the fourth projection data set and the second projection data set to a learned model functionalized to receive inputting of two projection data sets acquired from an identical target and output a high-quality projection data set, and generates the seventh projection data set by inputting the fifth projection data set and the third projection data set to the learned model.

10. The X-ray CT system according to claim 1, wherein the processing circuitry executes the second scanning by changing X-ray energy between the second X-ray energy and the third X-ray energy for each of one or a plurality of views.

11. The X-ray CT system according to claim 1, wherein the processing circuitry executes the second scanning by emitting X-rays of the second X-ray energy through a first X-ray tube and emitting X-rays of the third X-ray energy through a second X-ray tube.

12. The X-ray CT system according to claim 1, wherein the processing circuitry executes the second scanning by using a layered X-ray detector including a first layer that detects X-rays of the second X-ray energy and a second layer that detects X-rays of the third X-ray energy.

13. The X-ray CT system according to claim 1, wherein the processing circuitry executes the second scanning by using a first X-ray filter that attenuates an X-ray transmitting through the first X-ray filter to the second X-ray energy and a second X-ray filter that attenuates an X-ray transmitting through the second X-ray filter to the third X-ray energy.

14. The X-ray CT system according to claim 1, wherein the processing circuitry executes the second scanning by attenuating part of X-rays incident on the subject by using an X-ray filter that attenuates an X-ray transmitting through the X-ray filter from the second X-ray energy to the third X-ray energy.

15. A medical processing apparatus comprising processing circuitry configured to perform material decomposition among a plurality of reference materials based on: a fourth subject data set obtained based on a first subject data set corresponding to first X-ray energy and acquired by irradiating a first region of a subject with X-rays in first scanning and one of a second subject data set corresponding to second X-ray energy and a third subject data set corresponding to third X-ray energy different from the second X-ray energy, the second subject data set and the third subject data set being acquired by irradiating a second region included in the first region with X-rays in second scanning executed after the first scanning; and the other of the second subject data set and the third subject data set.

\* \* \* \* \*